US011974974B2

(12) United States Patent
Mei et al.

(10) Patent No.: US 11,974,974 B2
(45) Date of Patent: May 7, 2024

(54) CONTROLLED-RELEASE TABLETS, METHOD OF MAKING, AND METHOD OF USE THEREOF

(71) Applicant: Alvogen, Inc., Morristown, NJ (US)

(72) Inventors: Zhen Mei, Morristown, NJ (US); Amit Shah, Morristown, NJ (US); Mayank Joshi, Morristown, NJ (US); Raghav K. Gupta, Morristown, NJ (US)

(73) Assignee: ALVOGEN, INC., Morristown, NJ (US)

( * ) Notice: Subject to any disclaimer, the term of this patent is extended or adjusted under 35 U.S.C. 154(b) by 918 days.

(21) Appl. No.: 16/918,704

(22) Filed: Jul. 1, 2020

(65) Prior Publication Data
US 2021/0000775 A1    Jan. 7, 2021

Related U.S. Application Data
(60) Provisional application No. 62/870,121, filed on Jul. 3, 2019.

(51) Int. Cl.
| | | |
|---|---|---|
| A61K 31/197 | (2006.01) | |
| A61K 9/00 | (2006.01) | |
| A61K 9/20 | (2006.01) | |
| A61K 9/28 | (2006.01) | |

(52) U.S. Cl.
CPC .......... *A61K 31/197* (2013.01); *A61K 9/0065* (2013.01); *A61K 9/2027* (2013.01); *A61K 9/2095* (2013.01); *A61K 9/28* (2013.01)

(58) Field of Classification Search
CPC .. A61K 31/197; A61K 9/0065; A61K 9/2027; A61K 9/2095; A61K 9/28; A61K 9/2054
See application file for complete search history.

(56) References Cited

U.S. PATENT DOCUMENTS

| | | |
|---|---|---|
| 6,488,964 B2 | 12/2002 | Bruna et al. |
| 8,945,620 B2 | 2/2015 | Bockbrader et al. |
| 10,182,992 B2 | 1/2019 | Vamvakas et al. |
| 2002/0012679 A1 | 1/2002 | Bruna et al. |
| 2013/0078290 A1* | 3/2013 | Pilgaonkar ............ A61K 9/2027 514/561 |
| 2015/0250733 A1* | 9/2015 | Odidi .................... A61K 9/2886 514/561 |
| 2015/0283087 A1* | 10/2015 | Vamvakas ............ A61K 9/4875 424/452 |

FOREIGN PATENT DOCUMENTS

| | | |
|---|---|---|
| WO | 2008086492 A1 | 7/2008 |
| WO | 2010143052 A1 | 12/2010 |
| WO | 2010150221 A1 | 12/2010 |
| WO | 2011053003 A2 | 5/2011 |
| WO | 2011151708 A1 | 12/2011 |
| WO | 2012003968 A1 | 1/2012 |
| WO | 2013114281 A1 | 8/2013 |
| WO | 2013162114 A1 | 10/2013 |
| WO | 2014060952 A1 | 4/2014 |
| WO | 2015114509 A1 | 8/2015 |

OTHER PUBLICATIONS

Extended European Search Report for Application No. 20172176. 8-1109; dated Sep. 29, 2020; 8 pages.
DOW presentational materials "Using METHOCEL Cellulose Ethers for Controlled Release of Drugs in Hydrophilic Matrix Systems"; Distributed Mar. 27, 2019; 36 pages.
Fukuda, Mamoru et al.; "Floating hot-melt extruded tablets for gastroretentive controlled drug release system"; Journal of Controlled Release 115 (2006) 121-129.
Huda, I.G. et al; "Chewable Dispersible Tablet of Taste Masked Pregabalin"; International Journal of Pharmacy and Pharmaceutical Sciences; V. 5, Issue 4, 2013 ISSN: 0975-1491, p. 568-574.
Jadi, Rajendra Kumar et al.; "A Comprehensive Review on Gastroretentive Drug Delivery Systems"; Indo American Journal of Pharmaceutical Sciences; 2016: 3(2), p. 115-128; ISSN: 2349-7750: http://www.iajps.com.
Jeganathan et al; "Interpolyelectrolyte Complexes of Eudragit® EPO with Hypromellose Acetate Succinate and Eudragit® EPO with Hypromellose Phthalate as Potential Carriers for Oral Controlled Drug Delivery"; AAPS PharmSciTech, vol. 16, No. 4, Aug. 2015.
Kim et al. "Preparation and evaluation of non-effervescent gastroretentive tablets containing pregabalin for once-daily administration and dose proportional pharmacokinetics" International Journal of Pharmaceutics vol. 550, Issues 1-2, Oct. 25, 2018, pp. 160-169.
Lahoti, Swaroop Rameshwarji et al. "Development Optimization and In-vivo Evaluation of Swellable Gastroretentive Tablet by 32 Factorial Design"; Asian Journal of Pharmaceutics; Apr.-Jun. 2016, 10(2), 113, p. 1-11.
Lyrica CR Drug Information, 32 pages, Reference ID 4165845, Revised Oct. 2017.
M.P., Ratnaparkhi et al.; "Designing and In-Vitro Evaluation of Gastro Retentive Drug Delivery System for Pregabalin"; International Journal of PharmTech Research, Jul.-Sep. 2012, vol. 4, No. 3, pp. 1041-1049.
R. I. Moustafine et al. "Eudragit E PO as a Complementary Material for Designing Oral Drug Delivery Systems with Controlled Release Properties . . . " Mol. Pharmaceutics, 2013, 10 (7), pp. 2630-2641 Publication Date (Web): Jun. 3, 2013.
Thapa, Prakash et al.; "Effects of Formulation and Process Variables on Gastroretentive Floating Tablets with a High-Dose Soluble Drug and Experimental Design Approach"; Pharmaceutics, 2018, 10, 161 p. 1-25.
Yasir, Mohdet al.; "Biopharmaceutical Classifcation System: An Account"; Int.J. PharmTech Res. 2010, 2(3) pp. 1681-1690.

* cited by examiner

*Primary Examiner* — Anna R Falkowitz
(74) *Attorney, Agent, or Firm* — CANTOR COLBURN LLP

(57) ABSTRACT

Disclosed are gastroretentive, sustained-release tablet formulations comprising an active agent, such as pregabalin or a pharmaceutically acceptable form thereof, crospovidone, and a cationic copolymer based on dimethylaminoethyl methacrylate, butyl methacrylate, and methyl methacrylate random copolymer.

19 Claims, No Drawings

CONTROLLED-RELEASE TABLETS, METHOD OF MAKING, AND METHOD OF USE THEREOF

CROSS-REFERENCE TO RELATED APPLICATIONS

This application claims the benefit of U.S. Provisional Application No. 62/870,121 filed Jul. 3, 2019, which is hereby incorporated by reference in its entirety for all purposes.

BACKGROUND

The Biopharmaceutics Classification System (BCS) classifies drug substances according to four classes based upon their solubility and permeability. BCS Class I drug substances, such as metoprolol, paracetamol, and pregabalin, exhibit both high permeability and high solubility. Thus, BCS Class I drug substances are good candidates for controlled-release formulations, including sustained-release formulations. BCS Class I drugs in immediate-release formulations require multiple doses per day, and the controlled-release formulation would allow for reduced number of administrations and improved patient compliance.

Pregabalin, known by its chemical name (S)-3-isobutyl-gamma-aminobutyric acid, is absorbed from the small intestine and proximal colon. Pregabalin gastroretentive formulations have been developed in order to retain the formulation in the upper gastrointestinal tract to allow for sustained-release of pregabalin. Many of these formulations require complex bioadhesive systems and floating systems.

There remains a need in the art for new controlled-release formulations for BCS Class I drug substances, including new, simpler pregabalin formulations that exhibit sustained-release of the active agent for once-a-day administration.

SUMMARY

Disclosed herein is a non-effervescent gastroretentive, sustained-release tablet formulation, comprising pregabalin or a pharmaceutically acceptable form thereof; crospovidone; and a cationic copolymer based on dimethylaminoethyl methacrylate, butyl methacrylate, and methyl methacrylate random copolymer.

In another embodiment, a non-effervescent gastroretentive, sustained-release tablet formulation comprises about 29 to about 30 wt. % of pregabalin free form; about 21 to about 24 wt. % crospovidone; about 2.5 to about 2.75 wt. % of a cationic copolymer based on dimethylaminoethyl methacrylate, butyl methacrylate, and methyl methacrylate random copolymer; about 39 to about 41 wt. % hydroxypropyl methyl cellulose; and the balance is about 4 to about 6 wt. % of binder, filler, lubricant, glidant, or any combination thereof, wherein all the amounts are based on the total weight of core tablet.

In an embodiment, a non-effervescent gastroretentive, sustained-release tablet formulation comprises an active agent, specifically pregabalin or a pharmaceutically acceptable form thereof; crospovidone in an amount of about 20 to about 40 wt. %, specifically about 24 to about 36 wt. %, and yet more specifically about 28 to about 32 wt. %; a cationic copolymer based on dimethylaminoethyl methacrylate, butyl methacrylate, and methyl methacrylate random copolymer (e.g. EUDRAGIT E PO) in an amount of about 2.5 to about 5.0 wt. %, specifically about 3.0 to about 4.5 wt. %, and yet more specifically about 3.5 to about 4.0 wt. %; hydroxypropyl methyl cellulose controlled-release polymer in an amount of about 40 to about 74 wt. %, specifically about 45 to about 69 wt. %, and yet more specifically about 50 to about 63 wt. %; and the balance is binder, filler, lubricant, glidant, or any combination thereof, specifically in an amount of about 0.1 to about 11 wt. %, specifically about 2 to about 10 wt. %, and yet more specifically about 4 to about 9 wt. %; wherein the amounts are based on the total weight of the core tablet excluding the weight of the active agent (e.g. pregabalin).

In a further embodiment, a method of making the non-effervescent gastroretentive, sustained-release tablet formulation comprises wet granulating pregabalin with a controlled-release polymer, a binder, and a granulation liquid to form wet granulates; drying the wet granulates to form dried granulates; blending the dried granulates with crospovidone, a cationic copolymer based on dimethylaminoethyl methacrylate, butyl methacrylate, and methyl methacrylate random copolymer, and optionally a filler, a lubricant, a glidant or a combination thereof, to form a blend; and compressing the blend into core tablets.

In another embodiment, a method of treating a subject in need thereof comprises administering the non-effervescent gastroretentive, sustained-release tablet formulation described herein to the subject to treat neuropathic pain, epilepsy, fibromyalgia, or generalized anxiety disorder.

The above described and other features are exemplified by the following detailed description.

DETAILED DESCRIPTION

Disclosed herein are gastroretentive, sustained-release formulations of drug substances, specifically pregabalin or a pharmaceutically acceptable form thereof. The gastroretentive, sustained-release formulations are non-effervescent. The gastroretentive, sustained-release formulations of pregabalin or a pharmaceutically acceptable form thereof can be administered for once-a-day administration.

The gastroretentive, sustained-release tablet formulations of pregabalin or a pharmaceutically acceptable form thereof, generally comprise a matrix comprising pregabalin and a controlled-release composition. The controlled-release composition comprises crospovidone and a cationic copolymer based on dimethylaminoethyl methacrylate, butyl methacrylate, and methyl methacrylate random copolymer. These cationic copolymers are referred to as Amino Methacrylate Copolymer-NF according to USP/NF (United States Pharmacopeia (USP) and the National Formulary (NF)), Basic Butylated Methacrylate Copolymer of European Pharmacopoeia (Ph. Eur.), and Aminoalkyl Methacrylate Copolymer E of Japanese Pharmacopoeia (JPE). Commercially available cationic copolymer based on dimethylaminoethyl methacrylate, butyl methacrylate, and methyl methacrylate includes Evonik Industries' Eudragit® E PO, Eudragit® E 100, Eudragit® E 12,5, or a combination thereof having a ratio of dimethylaminoethyl methacrylate, butyl methacrylate, and methyl methacrylate of 2:1:1. It has been found that the use of a combination of crospovidone and a cationic copolymer based on dimethylaminoethyl methacrylate, butyl methacrylate, and methyl methacrylate random copolymer in a controlled release matrix, such as a diffusion controlled-release matrix prepared from a hydroxypropyl methyl cellulose, results in a gastroretentive, sustained-release formulation having enhanced properties. Such properties include allowing the composition to retain the active agent in the stomach for a longer duration of time than in the absence of the combination.

As used herein, "pregabalin or a pharmaceutically acceptable form thereof" includes pregabalin its free form (zwitterion), and its pharmaceutically acceptable complexes, salts, solvates, hydrates, and polymorphs. Exemplary salts include acid addition salts and base addition salts. Pharmaceutically acceptable acid addition salts may include salts derived from inorganic acids such as hydrochloric, nitric, phosphoric, sulfuric, hydrobromic, hydroiodic, hydrofluoric, phosphorous, and the like, as well as salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, and the like. Exemplary salts include acetate, aspartate, benzoate, chlorobenzoate, methylbenzoate, dinitrobenzoate, besylate, bicarbonate, carbonate, bisulfate, sulfate, pyrosulfate, bisulfite, sulfite, borate, camsylate, caprylate, citrate, edisylate, esylate, formate, fumarate, gluceptate, gluconate, glucuronate, hexafluorophosphate, hibenzate, hydrochloride, chloride, hydrobromide, bromide, hydroiodide, iodide, isethionate, isobutyrate, lactate, malate, maleate, malonate, mandelate, mesylate, methylsulfate, naphthylate, 2-napsylate, nicotinate, nitrate, orotate, oxalate, palmitate, pamoate, phosphate, hydrogen phosphate, dihydrogen phosphate, metaphosphate, pyrophosphate, phthalate, propionate, saccharate, sebacate, stearate, suberate, succinate, tartrate, tosylate, trifluoroacetate, and the like.

Pharmaceutically acceptable base salts of pregabalin may include nontoxic salts derived from bases, including metal cations, such as an alkali or alkaline earth metal cation, as well as amines. Examples of these salts include, aluminum, arginine, N,N'-dibenzylethylenediamine, calcium, chloroprocaine, choline, diethanolamine, diethylamine, dicyclohexylamine, ethylenediamine, glycine, lysine, magnesium, N-methylglucamine, olamine, potassium, procaine, sodium, tromethamine, zinc, and the like.

The pregabalin or a pharmaceutically acceptable form thereof can be present in the gastroretentive, sustained-release tablet formulation in an amount of about 2.0 to about 50 weight percent (wt. %), specifically about 9.0 to about 40 wt. %, and yet more specifically about 15 to about 30 wt. % of the total weight of the core tablet.

The pregabalin free form may be present in the gastroretentive, sustained-release tablet in an amount of about 50 milligrams (mg) to about 450 mg, specifically about 75 mg to about 350 mg, yet more specifically about 100 to about 275 mg per tablet. The pregabalin may be present in the gastroretentive, sustained-release tablet in an amount of about 82.5 mg, about 165 mg, or about 330 mg per tablet.

The crospovidone can be present in the gastroretentive, sustained-release tablet formulation in an amount of about 20 to about 40 wt. %, specifically about 24 to about 36 wt. %, and yet more specifically about 28 to about 32 wt. % of the total weight of the core tablet excluding the weight of the active agent (e.g. pregabalin).

The cationic copolymer based on dimethylaminoethyl methacrylate, butyl methacrylate, and methyl methacrylate random copolymer (e.g. EUDRAGIT E PO) can be present in the matrix of the gastroretentive, sustained-release tablet formulation in an amount of about 2.5 to about 5.0 wt. %, specifically about 3.0 to about 4.5 wt. %, and yet more specifically about 3.5 to about 4.0 wt. % of the total weight of the core tablet excluding the weight of the active agent (e.g. pregabalin).

The weight ratio of crospovidone to cationic copolymer based on dimethylaminoethyl methacrylate, butyl methacrylate, and methyl methacrylate random copolymer (e.g. EUDRAGIT E PO) in the tablet matrix can be about 6:1 to about 11:1, specifically about 7:1 to about 10:1, and yet more specifically about 8:1 to about 9:1.

The gastroretentive, sustained-release tablet formulation optionally further comprises an additional pharmaceutically acceptable excipient, such as a controlled-release polymer, a binder, a filler, a disintegrant, a lubricant, a glidant, or a combination thereof.

Suitable controlled-release polymers include hydroxypropyl methyl cellulose, including high molecular weight hydroxypropyl methyl cellulose having a molecular weight of about 4,000 to about 2,000,000, or 25,000 and above. Suitable commercially available controlled-release grades of hydroxypropyl methyl cellulose include those available from The Dow Chemical Company, specifically the METHOCEL Premium CR Grades (see Table 1). A single controlled-release grade of hydroxypropyl methyl cellulose can be used, or a combination of hydroxypropyl methyl cellulose of varying grades can be used (e.g., combination of METHOCEL K15M CR and K100 LV.

TABLE 1

| METHOCEL Premium Product Grade | K100 Premium LV CR | K4M Premium CR | K15M Premium CR | K100M Premium CR | E4M Premium CR | E10M Premium CR |
| --- | --- | --- | --- | --- | --- | --- |
| Methoxyl, % (USP) | 19-24 | 19-24 | 19-24 | 19-24 | 28-30 | 28-30 |
| Hydroxypropoxyl, % (USP) | 7-12 | 7-12 | 7-12 | 7-12 | 7-12 | 7-12 |
| Substitution type (USP/EP) | 2208 | 2208 | 2208 | 2208 | 2910 | 2910 |
| Apparent viscosity, 2% in water at 20° C., cP (USP) | 80-120 | 3000-5600 | 11250-21000 | 80000-120000 | 3000-5600 | 7500-14000 |
| Apparent viscosity, 2% in water at 20° C., mPa · s (EP) | 78-117 [98 Nom] | 2308-3755 [2903 Nom] | 6138-9030 [7382 Nom] | 16922-19267 [18243 Nom] | 2308-3755 [2903 Nom] | 4646-7070 [5673 Nom] |

The hydroxypropyl methyl cellulose controlled-release polymer can be present in the matrix of the gastroretentive, sustained-release tablet formulation in an amount of about 40 to about 74 wt. %, specifically about 45 to about 69 wt. %, and yet more specifically about 50 to about 63 wt. % of the total weight of the core tablet excluding the weight of the active agent (e.g. pregabalin).

Suitable binders include polyvinylpyrrolidone, hydroxypropyl cellulose, hydroxyethyl cellulose, methylcellulose, ethylcellulose, gum arabic, alginic acid and its derivatives, mannitol, lactose, starch, and the like.

Suitable fillers include a water insoluble filler, such as silicon dioxide, titanium dioxide, talc, alumina, starch, kaolin, polacrilin potassium, powdered cellulose, microcrystalline cellulose, and the like. Exemplary water-soluble fillers include water soluble sugars and sugar alcohols, specifically lactose, glucose, fructose, sucrose, mannose, dextrose, galactose, mannitol, sorbitol, xylitol, and the like.

Exemplary lubricants include lubricants include talc, calcium stearate, magnesium stearate, solid polyethylene glycols, sodium lauryl sulfate, glyceryl behenate, a combination thereof, and the like. In one aspect, the lubricant is magnesium stearate.

Exemplary glidants include colloidal silicon dioxide, starch, talc, a combination thereof, and the like.

The binder, filler, lubricant, glidant, or any combination thereof can be present in the matrix of the gastroretentive, sustained-release tablet formulation in an amount of about 0.1 to about 11 wt. %, specifically about 2 to about 10 wt. %, and yet more specifically about 4 to about 9 wt. % of the total weight of the core tablet excluding the weight of the active agent (e.g. pregabalin).

The gastroretentive, sustained-release tablet formulation may optionally further comprise a non-controlled-release coating, that is, an immediate-release coating, a color-identifying coating, a cosmetic coating, a seal coating, or the like. The non-controlled-release coating, optionally referred to as a non-functional coating, should not have an impact on the release of the active agent due to the initial dissolution, hydration, perforation of the coating, etc., and would not be considered to be a significant deviation from the non-coated formulation. Suitable non-controlled-release coating materials include immediate release film coating systems commercially available by COLORCON under the name OPADRY. Non-controlled-release coatings can include a water-soluble polymer, plasticizer, and optionally a pigment.

The gastroretentive, sustained-release tablet formulation is a non-effervescent gastroretentive tablet since it does not comprise an effervescent system typically found in effervescent gastroretentive formulations. Exemplary effervescent systems used in effervescent gastroretentive formulations include a gas generating agent typically to product carbon dioxide ($CO_2$), for example an alkali or alkaline earth metal carbonate, alkali or alkaline earth metal hydrogen carbonate (e.g., sodium bicarbonate), or a combination thereof. The effervescent system based on a gas generating agent may further comprise an acid such as an organic acid or organic acid salt (e.g., citric acid, tartaric acid, malic acid, fumaric acid, adipic acid, succinic acids, etc.).

The gastroretentive, sustained-release tablet formulation is not an orally dispersible tablet, but rather an oral tablet to be swallowed whole.

The gastroretentive, sustained-release tablet formulation is not an osmotic dosage form as it does not comprise an osmotic coating.

The gastroretentive, sustained-release tablet formulation can be prepared by combining the tablet matrix components with the active agent, specifically pregabalin, and forming into tablets by wet granulation of hydroxypropyl methyl cellulose (e.g., K15M Premium CR), binder and pregabalin, and then a blending of dried granulates with the remaining excipients followed by compression into core tablets. A suitable granulation liquid for the wet granulation is ethanol. The core tablet may then optionally be coated with a non-controlled-release coating as described herein.

In another aspect, the gastroretentive, sustained-release tablet formulation does not comprise a controlled-release coating. That is, it does not comprise a controlled-release coating that surrounds the outer surface of the matrix. If the gastroretentive, sustained-release tablet formulation includes an immediate-release coating, color-identifying coating, a seal coating, or the like (a non-controlled-release coating), it does not further comprise a controlled-release coating that surrounds the outer surface of that non-controlled-release coating.

By "controlled-release coating" is meant a coating in which the release of the active agent from the tablet is controlled or modified over a period of time for example, sustained-, delayed- or pulsed-release, due to the presence of that coating.

The gastroretentive, sustained-release tablet formulation can be for a twice-a-day administration, specifically for once-a-day administration. By "once-a-day administration" is meant administration once within a 24 hour period.

Although the gastroretentive, sustained-release tablet formulation has been described herein with pregabalin or a pharmaceutically acceptable form thereof as the active agent, the formulation is suitable for any active agent, specifically BCS Class I drug substances. Exemplary active agents include amitriptyline hydrochloride, biperiden hydrochloride, chloroquine phosphate, chlorpheniramine maleate, chlorpromazine hydrochloride, clomiphene citrate, cloxacillin sodium, cyclophosphamide, diazepam, diltiazem, divalproex sodium, doxycycline, ergotamine tartrate, fluconazole, fluoxetine, furosemide, gabapentin, indinavir sulfate, levamisole hydrochloride, levodopa, levothyroxine sodium, mefloquine hydrochloride, metformin, metoprolol, nelfinavir mesylate, neostigmine bromide, paracetamol, phenytoin sodium, prednisolone, promethazine hydrochloride, proguanil hydrochloride, propranolol, ranitidine hydrochloride, salbutamol, theophylline, valacyclovir, verapamil, warfarin sodium, and the like.

In an embodiment, a non-effervescent gastroretentive, sustained-release tablet formulation, comprises about 2.0 to about 50 wt. % of pregabalin free form based on the total weight of the core tablet; about 20 to about 40 wt. % crospovidone; about 2.5 to about 5.0 wt. % of a cationic copolymer based on dimethylaminoethyl methacrylate, butyl methacrylate, and methyl methacrylate random copolymer; about 40 to about 74 wt. % hydroxypropyl methyl cellulose; and the balance is binder, filler, lubricant, glidant, or any combination thereof, wherein the amounts for the crospovidone, cationic copolymer, and hydroxypropyl methyl cellulose are based on the total weight of core tablet excluding the weight of the pregabalin free form. Within this embodiment, the binder, filler, lubricant, glidant, or any combination thereof is present in an amount of about 0.1 to about 11 wt. % of the total weight of the core tablet excluding the weight of the pregabalin free form.

The gastroretentive, sustained-release tablet formulation can have a targeted dissolution profile. A dissolution profile is a plot of the cumulative amount of active agent released as a function of time. A dissolution profile can be measured utilizing, for example, standard test USP Test <711>.

The gastroretentive, sustained-release tablet formulations may be characterized by its dissolution properties. For testing, a USP test method 2 (paddle) apparatus, 50 rpm using acidic medium as the dissolution medium (e.g., 900 mL) at 37° C.±0.5° C. may be employed. Dissolution may also be tested at different pHs.

In an embodiment, a gastroretentive, sustained-release pregabalin tablet formulation exhibits a dissolution profile such that after combining the tablet with 900 ml of a 0.1 N HCl dissolution medium at 37° C.±0.5° C. according to USP 42<711> test method 2 (paddle), 50 rpm paddle speed, about 18 to about 24 wt. % of the total amount of pregabalin is released at 1 hour; about 30 to about 38 wt. % of the total amount of pregabalin is released at 2 hours; about 45 to about 55 wt. % of the total amount of pregabalin is released at 4 hours; and about 57 to about 67 wt. % of the total amount of pregabalin is released at 6 hours.

In an embodiment, a gastroretentive, sustained-release pregabalin tablet formulation exhibits a dissolution profile such that after combining the tablet with 900 ml of a pH 4.5 aqueous dissolution medium (e.g. acetate buffer) at 37° C.±0.5° C. according to USP 42 <711> test method 2 (paddle), 50 rpm paddle speed, about 39 to about 43 wt. % of the total amount of pregabalin is released at 6 hour; about 59 to about 64 wt. % of the total amount of pregabalin is released at 12 hours; about 69 to about 74 wt. % of the total amount of pregabalin is released at 16 hours; about 77 to about 83 wt. % of the total amount of pregabalin is released at 20 hours; and about 80 to about 90 wt. % of the total amount of pregabalin is released at 24 hours.

The gastroretentive, sustained-release pregabalin tablet formulations can be used in the treatment of neuropathic pain (pain due to nerve damage), including peripheral neuropathic pain, such as the pain experienced by diabetic patients or by patients who have had herpes zoster (shingles), and central neuropathic pain, such as the pain experienced by patients who have had a spinal-cord injury; epilepsy, as an 'add-on' to existing treatment in patients who have partial seizures (epileptic fits starting in one specific part of the brain) that cannot be controlled with their current treatment; fibromyalgia; or generalized anxiety disorder (long-term anxiety or nervousness about everyday matters). The gastroretentive, sustained-release pregabalin tablet formulation is administered once daily.

In an embodiment, gastroretentive, sustained-release pregabalin tablet formulations for use as a medicament, for example in the treatment of neuropathic pain associated with diabetic peripheral neuropathy or postherpetic neuralgia. A method of treating neuropathic pain associated with diabetic peripheral neuropathy or postherpetic neuralgia in a subject in need thereof comprises administering a gastroretentive, sustained-release pregabalin tablet formulation as disclosed herein to the subject. The gastroretentive, sustained-release pregabalin tablet formulation is administered once daily.

In an embodiment, gastroretentive, sustained-release pregabalin tablet formulations for use as a medicament, for example in the treatment of generalized anxiety disorder. A method of treating generalized anxiety disorder in a subject in need thereof comprises administering a gastroretentive, sustained-release pregabalin tablet formulation as disclosed herein to the subject. The gastroretentive, sustained-release pregabalin tablet formulation is administered once daily.

EXAMPLES

Example 1. Gastroretentive, Sustained-Release Pregabalin Tablet Formulations; Comparative Tablets A gastroretentive, sustained-release pregabalin tablet formulation was prepared (Form. 1 and Form. 1*, same general formulation, different batches) with the components listed in Table 2. The tablet matrix contained hydroxypropyl methyl cellulose, crospovidone, and EUDRAGIT E PO (Amino Methacrylate Copolymer-NF). Four comparative formulations were also prepared. Two comparative formulations were prepared as effervescent gastroretentive tablet formulations containing sodium bicarbonate and a hydroxypropyl methyl cellulose controlled-release matrix (Comp. A and Comp. B). Two additional comparative formulations were prepared as non-effervescent gastroretentive tablet formulations having a matrix containing polyethylene oxide, KOLLIDON SR, CARBOPOL, and crospovidone (Comp. C and Comp. D). The film coating on each tablet formulation and comparative tablet formulation is an immediate-release film coating.

TABLE 2

| Ingredients | Formulation | | | | | |
| --- | --- | --- | --- | --- | --- | --- |
| | Comp. A mg/tablet | Comp. B mg/tablet | Form. 1 mg/tablet | Form. 1* mg/tablet | Comp. C mg/tablet | Comp. D mg/tablet |
| Pregabalin | 330.0 | 330.0 | 330.0 | 330.0 | 330.0 | 330.0 |
| Polyethylene oxide, Molecular Weight 2,000,000 | — | — | — | — | 247.2 | 247.2 |
| Blend of polyvinyl acetate and povidone (K 30) in the ratio 8:2 (KOLLIDON SR) | — | — | — | — | 281.8 | 281.8 |
| Crospovidone | — | — | 249.5 | 249.5 | 302.9 | 302.9 |
| CARBOPOL | — | — | — | — | 61.8 | 61.8 |
| Hydroxypropyl methyl cellulose (METHOCEL K15MCR) | 200.0 | 300.0 | 350.0 | 350.0 | — | — |
| Hydroxypropyl methyl cellulose (METHOCEL K100 LV, low-viscosity grade) | — | — | 100.0 | 100.0 | — | — |
| EUDRAGIT E PO | — | — | 30.0 | 30.0 | — | — |
| Pregelatinized Starch | 150.0 | 150.0 | — | — | — | — |
| Microcrystalline Cellulose (AVICEL PH 101) | 180.0 | 80.0 | — | — | — | — |
| Sodium Bicarbonate USP | 82.5 | 82.5 | — | — | — | — |
| Hydroxypropylcellulose (KLUCEL EF) | 50.0 | 50.0 | 50.0 | 50.0 | — | — |
| Magnesium stearate | 5.0 | 5.0 | 10.0 | 10.0 | 9.3 | 9.3 |
| Collodial Silicon Dioxide | 2.5 | 2.5 | 2.5 | 2.5 | 3.0 | 3.0 |
| Film coating | 20.0 | 20.0 | 30.0 | 30.0 | 24.0 | 34.0 |
| Total | 1020.0 | 1020.0 | 1152.0 | 1152.0 | 1260.0 | 1270.0 |

*indicates a different batch of Form. 1.

Example 2. Dissolution

The gastroretentive, sustained-release pregabalin tablet formulations of Table 2. were analyzed in dissolution involving acidic media. Three different acidic media were used in the dissolution tests: 0.06 N HCl, 0.1 N HCl, and pH 4.5. Each test was conducted in 900 ml of the select dissolution medium at 37° C.±0.5° C. according to USP 42

<711> test method 2 (paddle), 50 rpm paddle speed. The results are provided in Tables 3. (0.06 N HCl), Table 4. (0.1 N HCl), and Table 5. (pH 4.5) below. A comparison with the dissolution of LYRICA CR tablets (330 mg) was performed.

As shown in the tables, Form. 1 exhibited good, slow release of pregabalin in acidic dissolution media. These tablets were closer to the release pattern of LYRICA CR in 0.1 N HCl compared to Comp. B, particularly in the first 6 hours. Form. 1 tablets were closer to the release pattern of LYRICA CR in pH 4.5 compared to Comp. A, particularly between hours 6 to 24.

TABLE 3

Dissolution: 0.06N HCl, 900 mL, Paddle, 50 rpm 0.06N HCl, 900 mL, Paddle, 50 rpm

| Time (hour) | Comp. A | Comp. B | Form. 1 | Form. 1* | Comp. C | Comp. D | Comp. E LYRICA CR |
|---|---|---|---|---|---|---|---|
| 0 | 0 | 0 | 0 | 0 | 0 | 0 | 0 |
| 1 | 17 | 14 | 18 | 19 | 22 | 19 | 19 |
| 2 | 28 | 23 | 28 | 29 | 34 | 29 | 29 |
| 4 | 44 | 37 | 43 | 43 | 51 | 44 | 44 |
| 6 | 56 | 48 | 54 | 53 | 62 | 56 | 56 |
| 9 | 71 | 61 | 66 | 68 | 75 | 69 | 69 |
| 12 | 83 | 73 | 76 | 77 | 83 | 78 | 78 |
| 16 | 93 | 84 | 85 | 86 | 91 | 87 | 87 |
| 20 | 100 | 93 | 92 | 93 | 96 | 93 | 94 |
| 24 | 103 | 98 | 96 | 97 | 99 | 97 | 97 |

TABLE 4

Dissolution: 0.1N HCl, 900 mL, Paddle, 50 rpm 0.1N HCl, 900 mL, Paddle, 50 rpm

| Time (hour) | Comp. A | Comp. B | Form. 1 | Form. 1* | Comp. C | Comp. D | Comp. E LYRICA CR |
|---|---|---|---|---|---|---|---|
| 0 | 0 | 0 | 0 | 0 | 0 | 0 | 0 |
| 1 | 19 | 16 | 19 | 19 | 24 | 21 | 20 |
| 2 | 29 | 25 | 31 | 30 | 38 | 32 | 32 |
| 4 | 44 | 39 | 46 | 45 | 55 | 48 | 48 |
| 6 | 57 | 50 | 57 | 57 | 67 | 59 | 60 |
| 8 | — | — | — | 66 | — | — | 69 |
| 9 | 73 | 64 | 69 | — | 79 | 72 | — |
| 10 | — | — | — | 74 | — | — | 77 |
| 12 | 84 | 75 | 79 | 80 | 86 | 81 | 83 |
| 14 | — | — | — | 85 | — | — | 87 |
| 16 | 93 | 86 | 87 | 89 | 93 | 89 | 91 |
| 18 | — | — | — | 93 | — | — | 94 |
| 20 | 99 | 94 | 93 | 95 | 97 | 95 | 96 |
| 22 | — | — | — | 97 | — | — | 97 |
| 24 | 101 | 99 | 97 | 99 | 99 | 98 | 98 |

TABLE 5

Dissolution: pH 4.5, 900 mL, Paddle, 50 rpm pH 4.5, 900 mL, Paddle, 50 rpm

| Time (hour) | Comp. A | Comp. B | Form. 1 | Form. 1* | Comp. C | Comp. D | Comp. E LYRICA CR |
|---|---|---|---|---|---|---|---|
| 0 | 0 | 0 | 0 | 0 | 0 | 0 | 0 |
| 1 | 17 | 12 | 14 | 13 | 15 | 11 | 10 |
| 2 | 24 | 19 | 21 | 20 | 21 | 18 | 17 |
| 4 | 36 | 30 | 31 | 31 | 33 | 30 | 28 |
| 6 | 46 | 39 | 40 | 40 | 43 | 39 | 37 |
| 8 | — | — | — | 49 | — | — | 45 |
| 9 | 59 | 50 | 50 | — | 55 | 50 | — |
| 10 | — | — | — | 55 | — | — | 52 |
| 12 | 69 | 60 | 59 | 62 | 64 | 60 | 58 |
| 14 | — | — | — | 67 | — | — | 63 |
| 16 | 81 | 71 | 69 | 73 | 74 | 71 | 68 |

TABLE 5-continued

Dissolution: pH 4.5, 900 mL, Paddle, 50 rpm pH 4.5, 900 mL, Paddle, 50 rpm

| Time (hour) | Comp. A | Comp. B | Form. 1 | Form. 1* | Comp. C | Comp. D | Comp. E LYRICA CR |
|---|---|---|---|---|---|---|---|
| 18 | — | — | — | 77 | — | — | 73 |
| 20 | 90 | 81 | 77 | 81 | 83 | 79 | 76 |
| 22 | — | — | — | 85 | — | — | 80 |
| 24 | 95 | 87 | 84 | 88 | 88 | 86 | 83 |

Example 3. Pharmacokinetic Study—Food Effect

A study was performed in healthy volunteers (17-18) to measure the area under the plasma/blood concentration-time curve (AUC) from time zero to time T (0-72 hours) or from time zero to infinity and (0-INF) and peak drug concentration ($C_{max}$) following single oral doses of pregabalin tablets as indicated in Table 5 in the fed and fasting state. For the fed state, the subjects were given a high-fat (approximately 50 percent of total caloric content of the meal) and high-calorie (approximately 800 to 1000 calories, with approximately 150, 250, and 500-600 calories from protein, carbohydrate, and fat, respectively. After administration of the doses, blood samples were taken from the subjects at approximately 1, 2, 3, 3.5, 4, 4.5, 5, 5.5, 6, 6.5, 7, 7.5, 8, 8.5, 9, 10, 11, 12, 14, 16, 24, 35.5, 48, 72 hours for the $1^{st}$ Bio Study. The results were calculated as the ratio between the two lots. The results are provided as a % ratio in Table 5.

TABLE 5

| | Comp. A vs. Comp. C | Comp. B vs. Comp. C | Form. 1 vs. Comp. D | Form. 1* vs. LYRICA CR |
|---|---|---|---|---|
| Fasting $C_{max}$ | 88.4 | 79.4 | 93.9 | 93.3 |
| $AUC_t$ | 87.3 | 77.4 | 105.7 | 92.2 |
| $AUC_{inf}$ | 87.2 | 77.7 | 105.5 | 92.3 |
| Fed $C_{max}$ | 133.6 | 113.1 | 101.4 | 99.5 |
| $AUC_t$ | 99.6 | 99.0 | 93.5 | 92.3 |
| $AUC_{inf}$ | 99.6 | 99.0 | 94.1 | 92.3 |

Comp. A and Comp. B effervescent tablets with a hydroxypropyl methylcellulose matrix show that increasing the controlled-release polymer hydroxypropyl methylcellulose correlates to slower drug release, and in turn, a lower $C_{max}$ at fasting. However, under fed study, both Comp. A and B showed higher $C_{max}$ than the reference (i.e. Comp. C). For Comp. A and B, the slower drug release in fasting and the faster drug release in fed comparing to reference (i.e. Comp. C) could indicate that the food effect for Comp. A & B is more significant than Comp. C. In order to reduce the food effect of Comp. A & B, Eudragit E PO is introduced into the formula (Form. 1). Eudragit E PO is soluble up to pH 5.0, swellable above pH 5.0. This increased the Cmax ratio between Form. 1 and reference Comp. D under fasting study and decreased the Cmax ratio between Form. 1 and reference Comp. D under fed study. Form 1/Form. 1* is non-effervescent tablet containing a matrix of hydroxypropyl methylcellulose, crospovidone, and EUDRAGIT E PO. Form. 1 is bioequivalent to LYRICA CR according to the FDA guidelines or criteria.

The compositions and methods disclosed herein include(s) at least the following aspects:

Aspect 1. A non-effervescent gastroretentive, sustained-release tablet formulation, comprising: pregabalin or a pharmaceutically acceptable form thereof; crospovidone; and a cationic copolymer based on dimethylaminoethyl methacrylate, butyl methacrylate, and methyl methacrylate random copolymer.

Aspect 2. The non-effervescent gastroretentive, sustained-release tablet formulation of Aspect 1, wherein crospovidone is present in an amount of about 20 to about 40 wt. %, specifically about 24 to about 36 wt. %, and yet more specifically about 28 to about 32 wt. % of the total weight of the core tablet excluding the weight of the pregabalin or pharmaceutically acceptable form thereof; and the cationic copolymer based on dimethylaminoethyl methacrylate, butyl methacrylate, and methyl methacrylate random copolymer is present in an amount of about 2.5 to about 5.0 wt. %, specifically about 3.0 to about 4.5 wt. %, and yet more specifically about 3.5 to about 4.0 wt. % of the total weight of the core tablet excluding the weight of the pregabalin or pharmaceutically acceptable form thereof.

Aspect 3. The non-effervescent gastroretentive, sustained-release tablet formulation of any one of Aspects 1-2, wherein the weight ratio of crospovidone to cationic copolymer based on dimethylaminoethyl methacrylate, butyl methacrylate, and methyl methacrylate random copolymer (e.g. EUDRAGIT E PO) in the tablet is about 6:1 to about 11:1, specifically about 7:1 to about 10:1, and yet more specifically about 8:1 to about 9:1.

Aspect 4. The non-effervescent gastroretentive, sustained-release tablet formulation of any one of Aspects 1-3, wherein the pregabalin or a pharmaceutically acceptable form thereof is present in an amount of about 2.0 to about 50 weight percent (wt. %), specifically about 9.0 to about 40 wt. %, and yet more specifically about 15 to about 30 wt. % of the total weight of the core tablet.

Aspect 5. The non-effervescent gastroretentive, sustained-release tablet formulation of any one of Aspects 1-4, comprising pregabalin free form present in an amount of about 50 milligrams (mg) to about 450 mg, specifically about 75 mg to about 350 mg, yet more specifically about 100 to about 275 mg per tablet.

Aspect 6. The non-effervescent gastroretentive, sustained-release tablet formulation of any one of Aspects 1-4, comprising pregabalin free form present in an amount of about 82.5 mg, about 165 mg, or about 330 mg per tablet.

Aspect 7. The non-effervescent gastroretentive, sustained-release tablet formulation of any one of Aspects 1-6, further comprising a controlled-release polymer, a binder, a filler, a disintegrant, a lubricant, a glidant, or a combination thereof.

Aspect 8. The non-effervescent gastroretentive, sustained-release tablet formulation of Aspect 7, wherein the controlled-release polymer is a hydroxypropyl methyl cellulose.

Aspect 9. The non-effervescent gastroretentive, sustained-release tablet formulation of any one of Aspects 7-8, wherein the controlled-release polymer is a hydroxypropyl methyl cellulose present in an amount of about 40 to about 74 wt. %, specifically about 45 to about 69 wt. %, and yet more specifically about 50 to about 63 wt. % of the total weight of the core tablet excluding the weight of the pregabalin or pharmaceutically acceptable form thereof.

Aspect 10. The non-effervescent gastroretentive, sustained-release tablet formulation of any one of Aspects 7-9, wherein the binder, filler, lubricant, glidant, or any combination thereof is present in an amount of about 0.1 to about 11 wt. %, specifically about 2 to about 10 wt. %, and yet more specifically about 4 to about 9 wt. % of the total weight of core tablet excluding the weight of the pregabalin or pharmaceutically acceptable form thereof.

Aspect 11. The non-effervescent gastroretentive, sustained-release tablet formulation of any one of Aspects 1-10, further comprising an immediate-release coating.

Aspect 12. A non-effervescent gastroretentive, sustained-release tablet formulation, comprising: about 29 to about 30 wt. % of pregabalin free form; about 21 to about 24 wt. % crospovidone; about 2.5 to about 2.75 wt. % of a cationic copolymer based on methylaminoethyl methacrylate, butyl methacrylate, and methyl methacrylate random copolymer; about 39 to about 41 wt. % hydroxypropyl methyl cellulose; and the balance is about 4 to about 6 wt. % of binder, filler, lubricant, glidant, or any combination thereof, wherein all the amounts are based on the total weight of core tablet.

Aspect 13. A non-effervescent gastroretentive, sustained-release tablet formulation, comprising an active agent, specifically pregabalin or a pharmaceutically acceptable form thereof; crospovidone in an amount of about 20 to about 40 wt. %, specifically about 24 to about 36 wt. %, and yet more specifically about 28 to about 32 wt. %; a cationic copolymer based on dimethylaminoethyl methacrylate, butyl methacrylate, and methyl methacrylate random copolymer (e.g. EUDRAGIT E PO) in an amount of about 2.5 to about 5.0 wt. %, specifically about 3.0 to about 4.5 wt. %, and yet more specifically about 3.5 to about 4.0 wt. %; hydroxypropyl methyl cellulose controlled-release polymer in an amount of about 40 to about 74 wt. %, specifically about 45 to about 69 wt. %, and yet more specifically about 50 to about 63 wt. %; and the balance is binder, filler, lubricant, glidant, or any combination thereof, specifically in an amount of about 0.1 to about 11 wt. %, specifically about 2 to about 10 wt. %, and yet more specifically about 4 to about 9 wt. %; wherein the amounts are based on the total weight of the core tablet excluding the weight of the active agent (e.g. pregabalin).

Aspect 14. The non-effervescent gastroretentive, sustained-release tablet formulation of any one of Aspects 1-13, wherein the tablet is free of a controlled-release coating and free of an osmotic coating.

Aspect 15. A method of making the non-effervescent gastroretentive, sustained-release tablet formulation of any one of Aspects 1-14, comprising wet granulating pregabalin with a controlled-release polymer (e.g., hydroxypropyl methyl cellulose), a binder, and a granulation liquid to form wet granulates; drying the wet granulates to form dried granulates; blending the dried granulates with crospovidone, a cationic copolymer based on dimethylaminoethyl methacrylate, butyl methacrylate, and methyl methacrylate random copolymer, and optionally a filler, a lubricant, a glidant or a combination thereof, to form a blend; and compressing the blend into core tablets.

Aspect 16. A method of treating a subject in need thereof, comprising:

administering the non-effervescent gastroretentive, sustained-release tablet formulation of any one of Aspects 1-14 to the subject to treat neuropathic pain, epilepsy, fibromyalgia, or generalized anxiety disorder.

Aspect 17. The method of Aspect 16, wherein the gastroretentive, sustained-release pregabalin tablet formulation is administered to the subject once daily.

Aspect 18. Use of the non-effervescent gastroretentive, sustained-release tablet formulation of any one of Aspects 1-14 to treat neuropathic pain, epilepsy, fibromyalgia, or generalized anxiety disorder in a subject in need thereof.

Aspect 19. The use of Aspect 18, wherein the gastroretentive, sustained-release pregabalin tablet formulation is administered to the subject once daily.

Aspect 20. The gastroretentive, sustained-release pregabalin tablet formulation of any one of Aspects 1-14 comprising 330 mg pregabalin exhibits a dissolution profile such that after combining the tablet with 900 ml of a pH 4.5 aqueous dissolution medium at 37° C.±0.5° C. according to USP <711> test method 2 (paddle), 50 rpm paddle speed, about 39 to about 43 wt. % of the total amount of pregabalin is released at 6 hour; about 59 to about 64 wt. % of the total amount of pregabalin is released at 12 hours; about 69 to about 74 wt. % of the total amount of pregabalin is released at 16 hours; about 77 to about 83 wt. % of the total amount of pregabalin is released at 20 hours; and about 80 to about 90 wt. % of the total amount of pregabalin is released at 24 hours.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

In general, the disclosure may alternately comprise, consist of, or consist essentially of, any appropriate components herein disclosed. The disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The endpoints of all ranges directed to the same component or property are inclusive of the endpoints, are independently combinable, and include all intermediate points and ranges (e.g., ranges of "up to 25 wt %, or more specifically 5 to 20 wt %" is inclusive of the endpoints and all intermediate values of the ranges of "5 to 25 wt %," such as "10 to 23 wt %," "20 to 24," "1 to 5 wt %," etc.). Disclosure of a narrower range or more specific group in addition to a broader range is not a disclaimer of the broader range or larger group.

"Combination" is inclusive of blends, mixtures, reaction products, and the like.

The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

Unless otherwise specified herein, any reference to standards, regulations, testing methods and the like, refer to the standard, regulation, guidance or method that is in force at the time of filing of the present application.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A non-effervescent gastroretentive, sustained-release tablet formulation, comprising a tablet matrix comprising:
    pregabalin or a pharmaceutically acceptable complex, salt, solvate, hydrate, or polymorph thereof;
    crospovidone present in an amount of about 20 to about 40 wt. % of the total weight of the tablet matrix excluding the weight of the pregabalin or a pharmaceutically acceptable complex, salt, solvate, hydrate, or polymorph thereof;
    a cationic dimethylaminoethyl methacrylate, butyl methacrylate, and methyl methacrylate random copolymer present in an amount of about 2.5 to about 5.0 wt. % of the total weight of the tablet matrix excluding the weight of the pregabalin or a pharmaceutically acceptable complex, salt, solvate, hydrate, or polymorph thereof; and
    a controlled-release polymer which is a hydroxypropyl methyl cellulose present in an amount of about 40 to about 74 wt. % of the total weight of the tablet matrix excluding the weight of the pregabalin or a pharmaceutically acceptable complex, salt, solvate, hydrate, or polymorph thereof.

2. The non-effervescent gastroretentive, sustained-release tablet formulation of claim 1, wherein
    crospovidone is present in an amount of about 24 to about 36 wt. % of the total weight of the tablet matrix excluding the weight of the pregabalin or a pharmaceutically acceptable complex, salt, solvate, hydrate, or polymorph thereof; and
    the cationic dimethylaminoethyl methacrylate, butyl methacrylate, and methyl methacrylate random copolymer is present in an amount of about 3.0 to about 4.5 wt. % of the total weight of the tablet matrix excluding the weight of the pregabalin or a pharmaceutically acceptable complex, salt, solvate, hydrate, or polymorph thereof.

3. The non-effervescent gastroretentive, sustained-release tablet formulation of claim 1, wherein the weight ratio of crospovidone to cationic dimethylaminoethyl methacrylate, butyl methacrylate, and methyl methacrylate random copolymer in the tablet is about 6:1 to about 11:1.

4. The non-effervescent gastroretentive, sustained-release tablet formulation of claim 1, wherein the pregabalin or a pharmaceutically acceptable complex, salt, solvate, hydrate, or polymorph thereof is present in an amount of about 2.0 to about 50 wt. % of the total weight of the tablet matrix.

5. The non-effervescent gastroretentive, sustained-release tablet formulation of claim 1, comprising pregabalin present in an amount of about 50 to about 450 mg per tablet.

6. The non-effervescent gastroretentive, sustained-release tablet formulation of claim 1, comprising pregabalin present in an amount of about 82.5 mg per tablet.

7. The non-effervescent gastroretentive, sustained-release tablet formulation of claim 1, further comprising a binder, a filler, a disintegrant, a lubricant, a glidant, or a combination thereof.

8. The non-effervescent gastroretentive, sustained-release tablet formulation of claim 1, wherein the controlled-release polymer is a hydroxypropyl methyl cellulose present in an amount of about 40 to about 69 wt. % of the total weight of the tablet matrix excluding the weight of the pregabalin or a pharmaceutically acceptable complex, salt, solvate, hydrate, or polymorph thereof.

9. The non-effervescent gastroretentive, sustained-release tablet formulation of claim 1, wherein the controlled-release polymer is a hydroxypropyl methyl cellulose present in an amount of about 45 to about 69 wt. % of the total weight of the tablet matrix excluding the weight of the pregabalin or a pharmaceutically acceptable complex, salt, solvate, hydrate, or polymorph thereof.

10. The non-effervescent gastroretentive, sustained-release tablet formulation of claim 7, wherein the binder, filler, lubricant, glidant, or any combination thereof is present in an amount of about 0.1 to about 11 wt. % of the total weight of tablet matrix excluding the weight of the pregabalin or a pharmaceutically acceptable complex, salt, solvate, hydrate, or polymorph thereof.

11. The non-effervescent gastroretentive, sustained-release tablet formulation of claim 1, further comprising an immediate-release coating.

12. A non-effervescent gastroretentive, sustained-release tablet formulation, comprising:
    a tablet matrix comprising
    about 29 to about 30 wt. % of pregabalin;
    about 21 to about 24 wt. % crospovidone;
    about 2.5 to about 2.75 wt. % of a cationic dimethylaminoethyl methacrylate, butyl methacrylate, and methyl methacrylate random copolymer;
    about 39 to about 41 wt. % hydroxypropyl methyl cellulose; and
    the balance is about 4 to about 6 wt. % of binder, filler, lubricant, glidant, or any combination thereof, wherein all the amounts are based on the total weight of tablet matrix.

13. A non-effervescent gastroretentive, sustained-release tablet formulation, comprising
a tablet matrix comprising
an active agent or a pharmaceutically acceptable complex, salt, solvate, hydrate, or polymorph thereof;
crospovidone in an amount of about 20 to about 40 wt. %;
a cationic dimethylaminoethyl methacrylate, butyl methacrylate, and methyl methacrylate random copolymer in an amount of about 2.5 to about 5.0 wt. %;
hydroxypropyl methyl cellulose controlled-release polymer in an amount of about 40 to about 74 wt. %; and
the balance is binder, filler, lubricant, glidant, or any combination thereof, in an amount of about 0.1 to about 11 wt. %;
wherein the amounts are based on the total weight of the tablet matrix excluding the weight of the active agent.

14. The non-effervescent gastroretentive, sustained-release tablet formulation of claim 13, wherein the active agent is pregabalin or a pharmaceutically acceptable complex, salt, solvate, hydrate, or polymorph thereof.

15. The non-effervescent gastroretentive, sustained-release tablet formulation of claim 1, wherein the tablet is free of a controlled-release coating and free of an osmotic coating.

16. A method of making the non-effervescent gastroretentive, sustained-release tablet formulation of claim 1, comprising
wet granulating pregabalin with a controlled-release polymer, a binder, and a granulation liquid to form wet granulates;
drying the wet granulates to form dried granulates;
blending the dried granulates with crospovidone, a cationic dimethylaminoethyl methacrylate, butyl methacrylate, and methyl methacrylate random copolymer, and optionally a filler, a lubricant, a glidant or a combination thereof, to form a blend; and
compressing the blend into tablets.

17. A method of treating a subject in need thereof, comprising:
administering the non-effervescent gastroretentive, sustained-release tablet formulation of claim 1 to the subject to treat neuropathic pain, epilepsy, fibromyalgia, or generalized anxiety disorder.

18. The method of claim 17, wherein the gastroretentive, sustained-release pregabalin tablet formulation is administered to the subject once daily.

19. The gastroretentive, sustained-release pregabalin tablet formulation of claim 1 comprising 330 mg pregabalin exhibits a dissolution profile such that after combining the tablet with 900 ml of a pH 4.5 aqueous dissolution medium at 37° C.±0.5° C. according to USP <711> test method 2 (paddle), 50 rpm paddle speed,
about 39 to about 43 wt. % of the total amount of pregabalin is released at 6 hour;
about 59 to about 64 wt. % of the total amount of pregabalin is released at 12 hours;
about 69 to about 74 wt. % of the total amount of pregabalin is released at 16 hours;
about 77 to about 83 wt. % of the total amount of pregabalin is released at 20 hours; and
about 80 to about 90 wt. % of the total amount of pregabalin is released at 24 hours.

* * * * *